(12) United States Patent
Gao et al.

(10) Patent No.: US 6,465,635 B2
(45) Date of Patent: *Oct. 15, 2002

(54) **PROMOTER SEQUENCE OF 3-PHOSPHOGLYCERATE KINASE GENE 1 OF LACTIC ACID-PRODUCING FUNGUS *RHIZOPUS ORYZAE* AND A METHOD OF EXPRESSING A GENE OF INTEREST IN FUNGAL SPECIES**

(75) Inventors: Johnway Gao, Richland, WA (US); Rodney S. Skeen, Pendleton, OR (US)

(73) Assignee: Battelle Memorial Institute, Richland, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/536,034

(22) Filed: Mar. 27, 2000

(65) Prior Publication Data

US 2002/0102636 A1 Aug. 1, 2002

(51) Int. Cl.$^7$ ................................................ C07H 21/04
(52) U.S. Cl. .................... 536/24.1; 435/69.1; 435/320.1
(58) Field of Search ............................. 435/91.4, 320.1, 435/484, 254.9; 536/24.1

(56) References Cited

FOREIGN PATENT DOCUMENTS

JP           3-247286    * 11/1991

OTHER PUBLICATIONS

CR Soccol et al. "Production of L–Lactic Acid by Rhizopus Species", p. 433–435, 1994.
MJ Haas et al. "Cloning, Expression and Characterization of a cDNA Encoding a Lipase From *Rhizopus Delemar*", p. 107–113, 1991.
P Yin et al. "Enhanced Production of L(+)–Lactic Acid From Corn Starch in a Culture of *Rhizopus Oryzae* Using an Air–Lift Bioreactor", p. 249–253. 1997.
P Van Solingen et al. "Sequence of the *Penicillium Chrysogenum* Phosphoglycerate Kinase Gene", p. 11823, 1988.
RA Hitzeman et al. "The Primary Structure of the *Saccharomyces Cerevisiae* Gene for 3–Phosphoglycerate Kinase", p. 7791–7808. 1982.
N Takaya et al. "Analysis of the 3–Phosphoglycerate Kinase 2 Promoter in *Rhizopus Niveus*", p. 121–125. 1995.
S Vanhanen et al. "Promoter Structure and Expression of the 3–Phosphoglycerate Kinase–Encoding Gene (pgk ) of *Trichoderma Reesei*", p. 129–133. 1991.
MJ Haas et al. "Lipases of the *Genera Rhizopus* and Rhizomucor: Versatile Catalysts in Nature and the Laboratory", p. 549–588. 1994.
N Takaya et al. "Cloning and Characterization of Two 3–Phosphoglycerate Kinase Genes of *Rhizopus Niveus* and Heterologous Gene Expression Using Their Promoters", p. 524–530. 1994.
DJ Ballance. "Transformation Systems for Filamentous Fungi and an Overview of Fungal Gene Structure", p. 1–29. 1991.
MG Richey et al. "Transformation of Filamentous Fungi with Plasmid DNA by Electroporation", p. 844–847. 1989.
M. Kapoor. "*Gene Transfer by Electroporation of Filamentous Fungi*", p. 279–289. 1996.
MJ Holland et al. "isolation and Identification of Yeast Messenger Ribonuclide Acids Coding for Enolase, Glyceraldehyde–3–Phosphate Dehydrogenase, and Phosphoglycerate Kinase", p. 4900–4907. 1978.
J Mellor et al. "Efficient Synthesis of Enzymatically Active Calf Chymosin in *Saccharomyces Cerevisiae*", p. 1–14. 1983.

* cited by examiner

Primary Examiner—Remy Yucel
Assistant Examiner—Bronwen M. Loeb
(74) Attorney, Agent, or Firm—Wells St. John P.S.

(57) ABSTRACT

The present invention provides the promoter clone discovery of phosphoglycerate kinase gene 1 of a lactic acid-producing filamentous fungal strain, *Rhizopus oryzae*. The isolated promoter can constitutively regulate gene expression under various carbohydrate conditions. In addition, the present invention also provides a design of an integration vector for the transformation of a foreign gene in *Rhizopus oryzae*.

11 Claims, 7 Drawing Sheets

FIG. 2

```
   1    tctcaaaccagtggctgctgaggttgaaaagcttttgggaaaacctgtcgaattcaagct   60
  61    tctgaggatgctattttagctgcaaagcatggttgtcaaggtattgtcatctctaaccat  120
 121    ggtggtagacaattggatttcgcaccttctgctattgaaattttgcctgaagtcacagct  180
 181    gctcttaagcgaggaagaattaatgaagaatttgaggtttatattgatggaggtattcga  240
 241    cgaggtagcgatattttaaagcaattgctttaggcgccaaaggtgtaggcattggacgt  300
 301    ccttctctggtaagcttgcgtaccttttaaagcaattgatatttaatgtgcgactagtat  360
 361    gctatgtcttcttatggtgatgctggtgtagaaaggctcttggaattattgcaggtaaat  420
 421    ttttttcacaattttggaaagaagctaactgaaaaatagaatgagtttgaaatgatcatg  480
 481    cgcttaatgggcgtaacatcgattgagcagattaagccagagatggtagatactcgtaat  540
 541    ctcaaggatcactttgcttctattcccaaggattatttggcagaattagcctatgatcca  600
 601    atgcaacctagatctcatttttctaagctataaaacaggaaaagatatcctttaaataaa  660
 661    gaacagcaatgttttctttcatcattgatgtacatacattatatttgtactatatgagca  720
 721    caacaatctatttatactgccttattacagtttagacaacttactgatactcattgatta  780
 781    ttctttgtacgcagacactaaccaaacacattagttttataccaacctgtgaattttata  840
 841    attcagcttgcttaagctttccaagtggcatggttttttctctgatgtcgcgatatcaaa  900
 901    attcaaaccgtatcacatctatcaaacaaaaaaaaggtgattccaagatgttatcaga  960
 961    aatatcaagctaggcttactttatgttattcgtttaggaagcttcattttttagaagaa 1020
1021    gaaaaaaagagttgaaaatacaaggaaacaagttaaatgttatacaataagcatgtgct 1080
1081    ttcataacagaaaggctcctttagtttaatgaaatcccgatttccatcgaacaatacc 1140
1141    aataatattatttgggaaagtgaagtcatgtatgattattttttctaatatttatgtca 1200
1201    agcaaatacttttcttctcttctctttaatttcaaataccaatttttcaacagaATG 1257
```

FIG. 3

```
RNPGK1:1                                                                    tacattatat  10
                                                                            || || ||
ROPK15:701                                                                  atatttgtac 710

RNPGK1:11    tatgtgagcataacaatctatttatattgctttattataacttagataacttactgatac   70
             ||| |||||||  ||||||||||||||| ||| ||||| |  ||||| |||||||||||||
ROPK15:711   tatatgagcacaacaatctatttatactgccttattacagtttagacaacttactgatac   770

RNPGK1:71    gcattgattattctttgtacgcagacactaaccaaacacgttagctttataccbacctgt   130
             |||||||||||||||||||||||||||||||||||||||| |||| |||||||| ||||||
ROPK15:771   tcattgattattctttgtacgcagacactaaccaaacacattagttttataccaacctgt   830

RNPGK1:131   gaatttTataattcagcttgcttaagctttccaagtggcatggttttttctctgatgtcg   190
             ||||||||||||||||||||||||||||||||||||||||||||||||||||||||||||
ROPK15:831   gaatttTataattcagcttgcttaagctttccaagtggcatggttttttctctgatgtcg   890

RNPGK1:191   cgatatcaaaattcaagaccgtatcacatTtatcaaacaaaaaaaaaaggtgactccaag   250
             |||||||||||||||||| ||||||||||| |||||||| |||||||||||||| ||||||
ROPK15:891   cgatatcaaaattcaaaaccgtatcacatctatcaaac-aaaaaaaaaggtgattccaag   949

RNPGK1:251   atgttatcagaaatatcaagccaagtttac-tttatattattcgtttaggaagcttcatt   309
             ||||||||||||||||||||||  |  |||| |||| ||||| |||||||||||||||||
ROPK15:950   atgttatcagaaatatcaagctaggcttacttttatgttattcgtttaggaagcttcatt   1009

RNPGK1:310   ttttagaagaagaaaaaaaagaaagttgaaaatacaaggaaacaagttaaatgttatac   369
             |||||||||||||||||||   | |||||||||||||||||||||||||||||||||||
ROPK15:1010  ttttagaagaagaaaaaaa---agagttgaaaatacaaggaaacaagttaaatgttatac   1066

RNPGK1:370   aataagcatgtgctttcataacagaaaggctcctttagtttaatgaaatcccgatttcca   429
             ||||||||||||||||||||||||||||||||||||||||||||||||||||||||||||
ROPK15:1067  aataagcatgtgctttcataacagaaaggctcctttagtttaatgaaatcccgatttcca   1126

RNPGK1:430   tcgaacaattacccaataatatcatttgggaaagtgaagtcatgtatgattatttttttc   489
             |||||||||||||||||||||| |||||||||||||||||||||||||||||||||||||
ROPK15:1127  tcgaacaattacccaataatattatttgggaaagtgaagtcatgtatgattatttttttc   1186

RNPGK1:490   t--tatttatgtcaagcaaatattttcttctcttctctttaatttcaaataccaatttt   547
             |  |||||||||||||||||| |||||||||||||||||||||||||||||||||||||
ROPK15:1187  taatatttatgtcaagcaaatacttttcttctcttctctttaatttcaaataccaatttt   1246

RNPGK1:548   ccaacagaATG   558
             |||||||||||
ROPK15:1247  tcaacagaATG   1257
```

PROMOTER SEQUENCE OF 3-PHOSPHOGLYCERATE KINASE GENE 1 OF LACTIC ACID-PRODUCING FUNGUS *RHIZOPUS ORYZAE* AND A METHOD OF EXPRESSING A GENE OF INTEREST IN FUNGAL SPECIES

This invention was made with Government support under Contract DE-AC0676RLO1830 awarded by the U.S. Department of Energy. The Government has certain rights in the invention.

FIELD OF THE INVENTION

The present invention is a promoter sequence of 3-phosphogycerate kinase gene 1 of lactic acid-producing fungus *Rhizopus oryzae* and a method of expressing a gene of interest in fungal species.

BACKGROUND OF THE INVENTION

The genus of Rhizopus is versatile in the production of biocatalysts such as glucoamylase and lipase and chemicals including L-(+)-lactic acid, fumaric acid, and ethanol. Rhizopus is the member of the order Mucorales, which is within the class Zygomycetes of the division Amastigomycota. *Rhizopus oryzae* (ATCC 9363) is the best lactic acid producer found in the Rhizopus genus, while *Rhizopus delemar* and *Rhizopus niveus* can produce significant amount of extracellular lipase. In addition, *R. oryzae* can also secrete large amount of glucoamylase in the solid culture for starch hydrolysis. Therefore, *R. oryzae* could be potentially a host for upgrading lactic acid production as well as foreign protein production. However, in the current literature, there is very limited information available on gene clones as well as gene regulatory elements (promoters) for *R. oryzae*. Less than nine gene clone and partial gene sequences are reported for *R. oryzae*, which include glucoamylase, ribosomal genes, and aspartic proteinase genes.

The ability to genetically manipulate filamentous fungi largely depends on the successfulness to develop the transformation methods and gene expression systems. Transformation methods have been developed for filamentous fungi, in particular, *Aspergillus nidulans* and *Neurospora crassa*, including others such as *Aspergillus niger*, *Aspergillus oryzae*, *Penicillium nalgiovense*. To effectively direct the transcription or expression of an interested gene, strong gene regulating elements or promoters are required. These promoters can be isolated from the upstream sequences of strongly expressed gene clones. Phosphoglycerate kinase gene is one of the highly expressed genes found in yeast and filamentous fungi. This gene encodes some of the most abundant mRNA in the yeast cells, accounting for up to 5% of the total cellular protein expression. After the discovery and characterization of *Saccharomyces cerevisiae* gene, other phosphoglycerate kinase genes were also isolated from various fungal species such as *Penicillium chrysogenum* and *Rhizopus niveus* using *S. cerevisiae* phosphoglycerate kinase gene as homologous gene probe. However, only a few of phosphoglycerate kinase gene promoters were isolated and characterized, which were from *S. cerevisiae*, *Trichoderma reesei*, and *R. niveus*, among others.

To genetically manipulate *R. oryzae*, either for the purpose of metabolic pathway modification, conferring necessary traits such as acid tolerance and upgrading of lactic acid production, or producing biocatalyst of interest, high levels of mRNA expression are always desirable. Therefore, there is a need to isolate strong promoter sequences of *R. oryzae* and design/develop expression vectors, harboring the isolated phosphoglycerate kinase gene promoter.

SUMMARY OF THE INVENTION

The present invention provides the promoter clone discovery of phosphoglycerate kinase gene 1 of a lactic acid-producing filamentous fungal strain, *Rhizopus oryzae*. The isolated promoter can constitutively regulate gene expression under various carbohydrate conditions. In addition, the present invention also provides a design of an integration vector for the transformation of a foreign gene in *Rhizopus oryzae*.

DESCRIPTION OF THE PREFERRED EMBODIMENT(S)

The present invention presents a promoter discovered in a fungal strain, *R. oryzae*, which is a lactic acid producing organism. The discovered promoter is related to the 3-phosphoglycerate kinase gene 1 (pgk1) promoter. The isolated promoter clone, SEQ ID: 7, has a length of 1257 base pairs prior to the pgk1 gene initiation codon. The present invention also shows that the *R. oryzae* pgk1 promoter is a constitutive promoter, which can regulate pgk1 gene expression in various media containing starch, glucose, mannose, galactose, xylose, and arabinose, respectively. In addition, the *R. oryzae* gene 1 has a mature transcription size of about 2.0 kb, based on the Northern blot analysis. This is different from the deduced open reading frame 1251 base pairs of pgk1 gene discovered in *R. niveus*. Further, as compared to the known upstream of *R. niveus* pgk1 gene sequence, SEQ ID: 8, from 1 to 555 base pairs, the *R. oryzae* pgk1 promoter sequence, SEQ ID: 9, from 701 to 1254 base pairs has a significant difference of 34 base pairs. In addition, the *R. oryzae* pgk1 promoter has an important TATA box (TAATA) located upstream of ATG at 1187 bp, while the *R. niveus* pgk1 gene does not have this TATA box at this position. Furthermore, this invention presents a design of a transformation vector for the fungal strain, *R. oryzae*, which utilizes the native pgk1 promoter to regulate the antibiotic (blasticidin) resistance gene of *Aspergillus terreus* in *R. oryzae*. This vector can potentially be used as a chromosomal integration vector for other foreign gene expression in *R. oryzae*. Another objective of the current invention is to use the *R. oryzae* pgk1 promoter to regulate foreign gene expression in other fungal species and plants.

For a clear and concise understanding of the specification and claims, including the scope given to such terms, the following definitions are provided:

PROMOTER: The expression of a gene is directed by a promoter, which is a DNA sequence and locates in the 5' region of a gene. A fungal promoter is a promoter sequence that will direct the transcription of a gene in fungal cells.

CONSTITUTIVE PROMOTER: The rate of gene transcription under such promoter is not regulated by an inducing agent, which can be a chemical compound, or a carbohydrate.

INDUCIBLE PROMOTER: an inducing agent regulates the rate of gene transcription under such promoter.

PLASMID VECTOR: A DNA plasmid vector contains a replicon or an origin of replication able to autonomously replicate the plasmid DNA in the original host organism. A plasmid vector can also serve as both a cloning vector for DNA manipulation in a bacterial host and a shuttle plasmid vector for interested DNA expression in another host cell.

CLONING PLASMID VECTOR: Cloning vectors typically contain one or a small number of restriction endonuclease recognition sites at which interested DNA sequences can be inserted for DNA manipulation purposes. Cloning vectors also contain a marker gene that is suitable for use in the identification and selection of cells transformed with the cloning vector. Marker genes typically include genes that provide tetracycline resistance or ampicillin resistance.

SHUTTLE PLASMID VECTOR: Shuttle plasmid vectors are plasmid vectors that contain two replicons; one of which replicates plasmid vector in a bacterial host cell for DNA manipulation; and the other replicates plasmid vector in another host cell for gene expression. The shuttle plasmid vector typically contains two selectable marker genes; one of which is usually an ampicillin resistance gene or tetracycline resistance used for selection of cells transformed with the vector during DNA manipulation; and the other is usually an anti-fungal antibiotic resistance gene used for the selection of expression host cells transformed with the vector. A shuttle plasmid vector can also be an expression vector and normally contains an expression cassette (promoter//multiple cloning sites// transcription terminator) in which a gene of interest can be inserted.

CHROMOSOMAL INTEGRATION VECTOR: A chromosomal integration vector is a plasmid vector which is able to integrate the whole plasmid DNA or part of the interested DNA into the cell chromosomal DNA. The chromosomal integration is due to recombination of homologous DNA fragment into the cell chromosome by efficient DNA repairing mechanism during fungal transformation. A chromosomal integration vector can also be an expression vector and normally contains an expression cassette (promoter//multiple cloning sites//transcription terminator) in which a gene of interest may be inserted for gene expression or promoter characterization. An expression vector construct can comprise a sequence of the DNA segment that is transcribed during the native expression of the gene of interest (transcription region). Such transcription region can be inserted downstream of the vector's expression cassette promoter and thereby placed under transcriptional control of the vector's promoter.

EXAMPLE 1
PCR Cloning of Phosphoglycerate Kinase 1 Promoter of *R. Oryzae*

Figure 1:
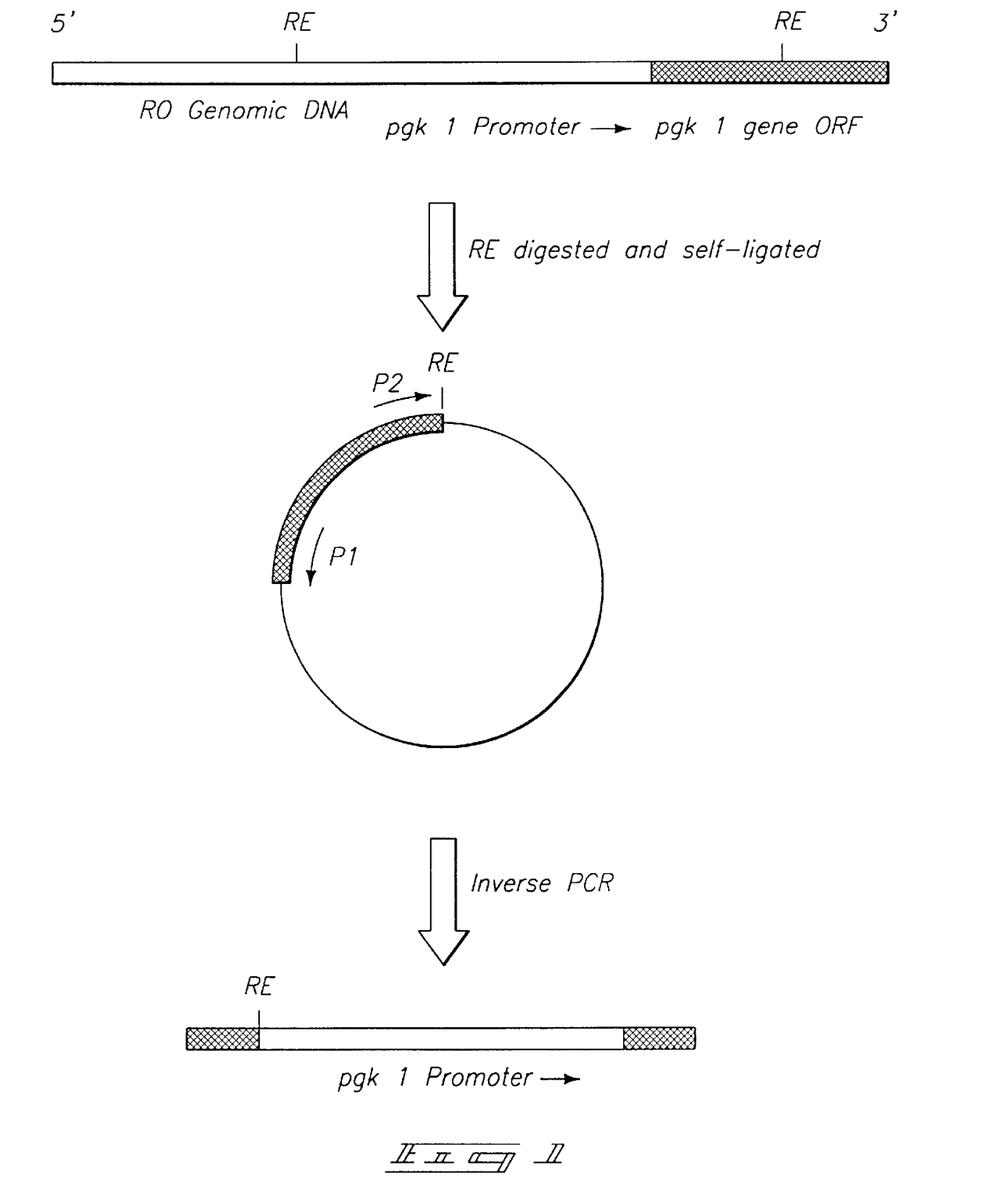
FIG. 1 is a graphic illustrating an inverse PCR method for promoter clone isolation.

To isolate the phosphoglycerate kinase 1 (pgk1) promoter from *R. oryzae* (ATCC 9363), the *R. oryzae* mycelium was grown overnight in a culture medium containing yeast extract 1%, peptone 2%, and potato starch 2%. Cells were then harvested and genomic DNA was isolated and purified from the culture. Inverse PCR method was used to clone out the promoter region, as shown in FIG. 1 where P1 is PCR reverse primer 1; P2 PCR forwarding primer 2; RE restriction enzyme site which can be cleaved both upstream of the pgk1 promoter and inside of the pgk1 gene; RO *Rhizopus oryzae*. PCR primers for the inverse PCR were designed based on the open reading frame of the pgk1 gene sequence of *Rhizopus niveus* under the assumption that pgk1 gene of *R. oryzae* and *R. niveus* is homologous. A 5' end over-hung sequence (italics) was designed to adapt restriction enzyme sites (underlined) such as Xba I and Sph I. The inverse PCR primers are listed as following:

Reverse primer PGK1-C-97; SEQ ID 1: GC TCT AGA AGG TTG AGG TCG CGA ATA GAG AGC TTG Reverse primer PGK2-C-98; SEQ ID 2: GC TCT AGA ACG GTA GGA AGA GCT TGA ACG ATA CGA Forwarding primer PGK3-N-99; SEQ ID 3: GAT GCA TGC TCT CAA ACC AGT GGC TGC TGA GGT TGA Forwarding primer PGK4-N-100; SEQ ID 4: GAT GCA TGC GCC TTT GGT ACT GCT CAC CGT GCT CAC Forwarding primer PGK5-N-101; SEQ ID 5: GAT GCA TGC TGT TAA AGT AAG GTT CTC TTA TAA Forwarding primer PGK6-N-102; SEQ ID 6: GAT GCA TGC TAT TTG AAT TCG ATG CCT TCT CTA The genomic DNA is first digested with different restriction enzymes, including Bgl II, EcoR I, Hinc II, Kpn I, Nco I, Sph I, and Xmn I, which locate within the 5' region the pgk1 gene of *R. niveus*. After digestion, the DNA samples are then purified and self-ligated using T4 DNA ligase. Table 1 shows the reverse PCR reaction matrix, which pairs various sets of reverse primer and forwarding primer together.

TABLE 1

Inverse PCR primer pair sets correspondent to each restriction enzyme digested DNA sample for the isolation of 3-phosphoglycerate kinase 2 promoter.

| PCR reaction No. | Restriction enzyme used for DNA digestion | Inverse PCR primer pairing |
| --- | --- | --- |
| 1 | Bgl II | PGK1-C-97; PGK1-C-101 |
| 2 | Bgl II | PGK1-C-98; PGK1-C-101 |
| 3 | EcoR I | PGK1-C-97; PGK1-C-99 |
| 4 | EcoR I | PGK1-C-98; PGK1-C-99 |
| 5 | Hinc II | PGK1-C-97; PGK1-C-100 |
| 6 | Hinc II | PGK1-C-98; PGK1-C-100 |
| 7 | Kpn I | PGK1-C-97; PGK1-C-102 |
| 8 | Kpn I | PGK1-C-98; PGK1-C-102 |
| 9 | Nco I | PGK1-C-97; PGK1-C-100 |
| 10 | Nco I | PGK1-C-98; PGK1-C-100 |
| 11 | Sph I | PGK1-C-97; PGK1-C-99 |
| 12 | Sph I | PGK1-C-98; PGK1-C-99 |
| 13 | Xmn I | PGK1-C-97; PGK1-C-99 |
| 14 | Xmn I | PGK1-C-98; PGK1-C-99 |

Figure 2:
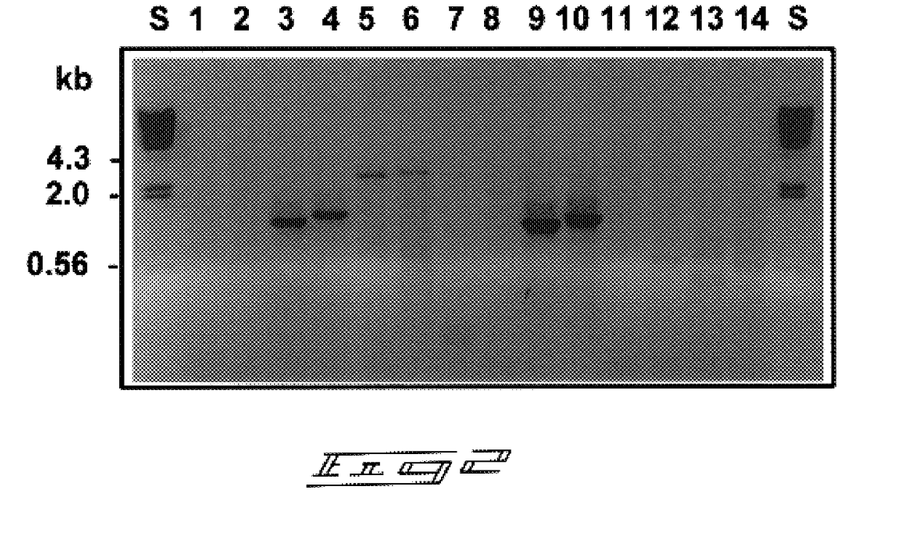
FIG. 2 is a graphic of a reverse gel image of PCR clones of *R. oryzae* phosphoglycerate kinase 1 promoter.

The inverse PCR reactions were conducted based on the primer pairing outlined in Table 1. After PCR reaction, the PCR products were separated in an agarose gel by electrophoresis. The inverse PCR results are shown in a reverse gel image in FIG. 2, where lane number is correspondent to each inverse PCR reaction in Table 1 and lane Hλ is the DNA size marker. The isolated pgk1 promoter clones are indicated as dark bands in the gel picture. Lanes 3, 4, 5, 6, 9, and 10 show strong bands, which correspondent to the ligated DNA samples previously cleaved by EcoR I, Hinc II, and Nco I, respectively. The sizes of the PCR clones range from about 1.0 kb to 3.0 kb.

EXAMPLE 2
Nucleotide Sequence of pgk1 Promoter Sequence

Figure 3:
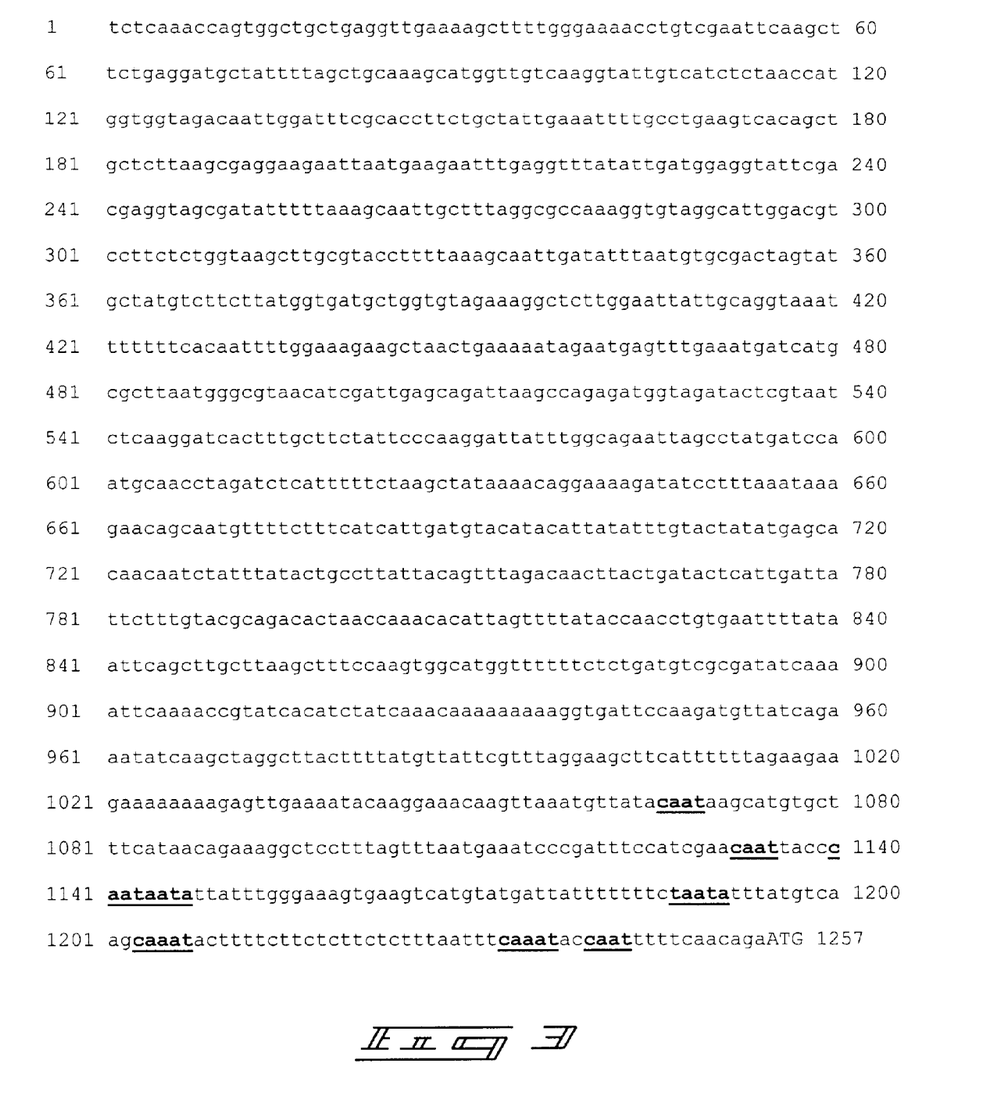
FIG. 3 is a graphic illustrating the sequence of a phosphoglycerate kinase 1 promoter of *R. oryzae*, SEQ ID: 7.

PCR product No.3 contains most of the pgk1 gene upstream sequence since the restriction enzyme EcoR I used to cleave the genomic DNA locates closer to the initial codon ATG than other restriction enzymes, Hinc II and Nco I, which locate further down stream of EcoR 1 site. The pgk1 promoter clone No. 3 was cloned into a vector pGEM-T (Promega, Madison, Wis.) to form pGA2086. Individual colonies were picked to confirm DNA insertion. Two of the individual clones, pGA2086a and pGA2086b, were completely sequenced from both ends. By sequence blasting, the overlapping sequence of these two clones indicated that they are identical and belong to one gene sequence. The complete nucleotide sequence of pgk1 gene promoter is shown in FIG. 3; SEQ ID 7. The cloned pgk1 promoter sequence has a length of 1257 bp. The putative TATA box and CAT box are bold and underlined. There are six CAT boxes and two TATA boxes within 200 base pairs upstream of the initial codon.

Figure 4:
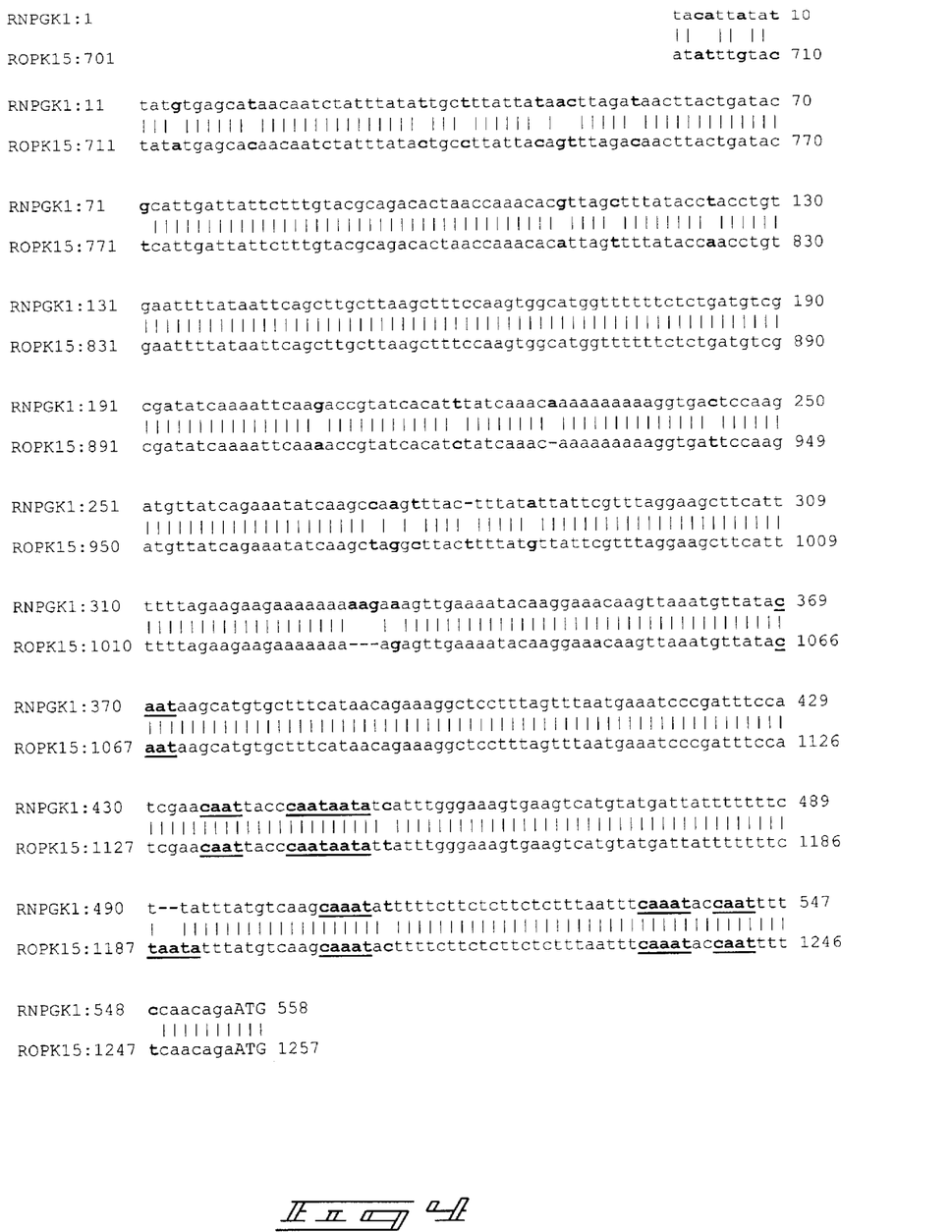
FIG. 4 is a graphic illustrating the homologous comparison of phosphoglycerate kinase 1 promoter sequences between *R. oryzae*, SEQ ID: 9 and *R. niveus*, SEQ ID: 8.

EXAMPLE 3
Homologous Comparison of pgk1 Promoter Sequence Between R. oryzae and R. niveus To compare the homology of pgk1 promoter between R. oryzae and R. niveus, promoter sequences from both origins were blasted against each other. The comparison results of pgk1 promoter are shown in FIG. 4, where ROPK15 is R. oryzae pgk1 promoter sequence, SEQ ID: 9; RNPGK1 is R. niveus pgk1 promoter sequence, SEQ ID: 8. The bold letters indicate the difference of both sequences and "–" indicates missing nucleotides of both sequences. ATG is the putative initial codon of pgk1 gene. Results indicate that there are 34 nucleotides of R. oryzae pgk1 promoter different from the pgk1 promoter of R. niveus. Within the 200 base pairs upstream of ATG, R. oryzae pgk1 promoter has two TATA boxes while the one of R. niveus has only one TATA box. R. niveus does not have the TATA box at 1187 base pair as shown in FIG. 4. These results conclude that the pgk1 promoter sequences of R. oryzae are not identical to the one isolated from R. niveus even though they are highly homologous.

EXAMPLE 4
Expression Patterns of pgk1 Gene in R. oryzae

Figure 5:
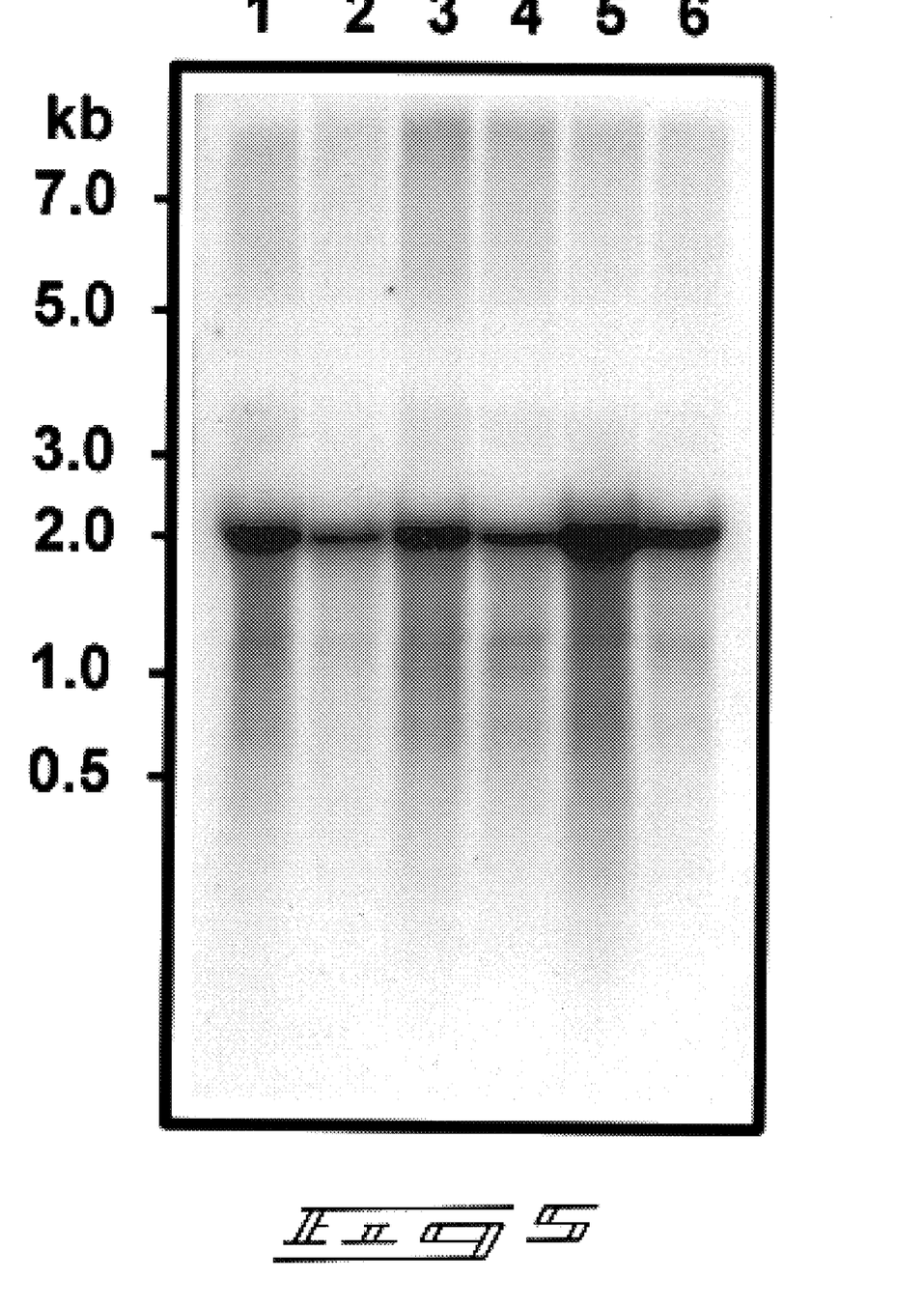
FIG. 5 is a graphic illustrating the expression of phosphoglycerate kinase 1 gene under different conditions.

To test the regulatory patterns of the pgk promoter, R. oryzae was grown in different culture media containing glucose, starch, xylose, mannose, galactose, and arabinose, respectively. Total RNA was isolated from the mycelia biomass using an RNeasy Maxi kit (QIAGEN Inc., Valencia, Calif.). Total RNA samples (50 μg per lane) were separated in 1.3% formaldehyde-agarose gel and capillary-blotted onto Zeta-Probe membrane (Bio-Rad Laboratories, Hercules, Calif.), which was then baked at 80° C. in a vacuum oven for two hours. Northern blot were hybridized with a $\alpha^{32}$P-dCTP labeled pgk1 gene probe. The Northern blot analysis results are shown in FIG. 5, where lane 1, 2, 3, 4, 5, and 6 are total RNA samples prepared from R. oryzae cultures grown in the medium with glucose, potato starch, xylose, mannose, galactose, and arabinose, respectively. The Northern blot indicates that R. oryzae phosphoglycerate kinase 1 gene has a mature RNA size of about 2 kb, different from the open reading frame (1.25 kb) of R. niveus pgk1 gene reported by indicating that pgk1 gene of R. oryzae is different from the one of R. niveus. R. oryzae pgk1 gene expresses in all the conditions tested, indicating that pgk1 promoter is a constitutive promoter. The strong expression was obtained in the medium containing galactose, glucose, and xylose, followed by arabinose, mannose and potato starch.

EXAMPLE 5
Transformation Vector Design for R. oryzae

Figure 6:
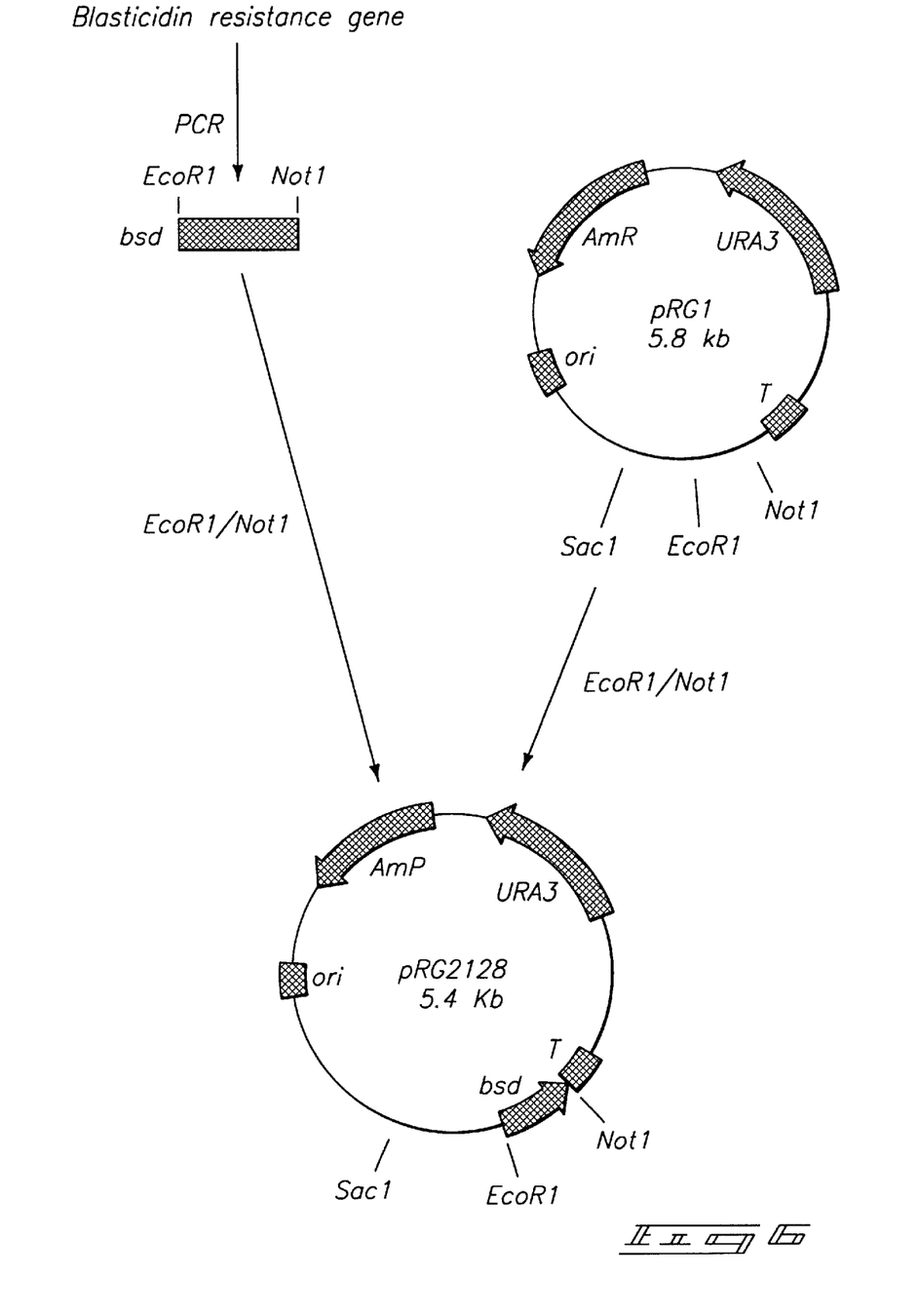
FIG. 6 is a graphic illustrating a plasmid vector pGA2128 construction.
Figure 7:
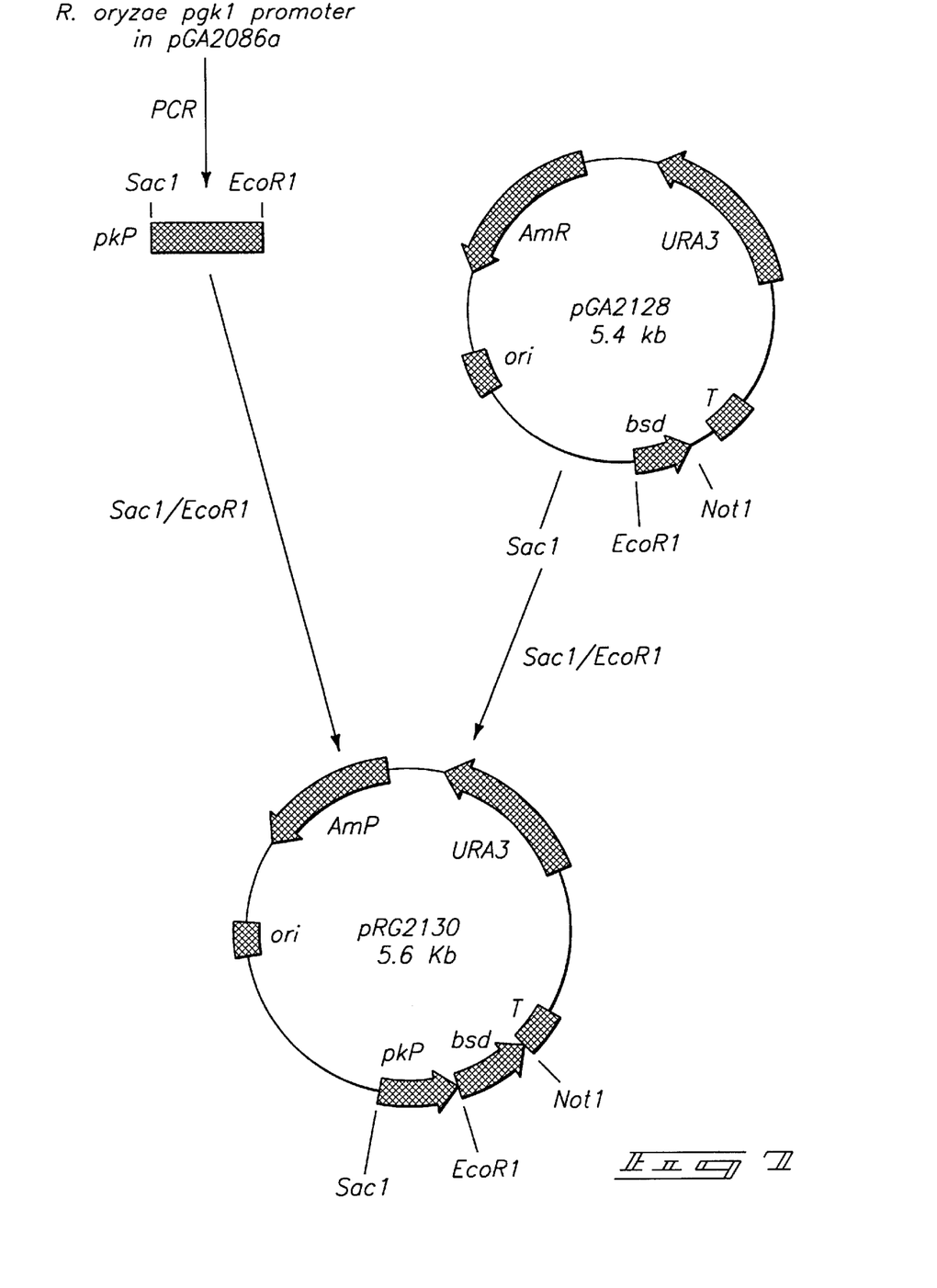
FIG. 7 is a graphic illustrating a plasmid vector pGA2130 construction for *R. oryzae* transformation.

To develop transformation vector system for foreign gene expression in R. oryzae, the following vector is designed. A blasticidin resistance gene (Invitrogen, Carlsbad, Calif.) was first cloned out by PCR, and cloned into pGEM-T vector (Promega, Madison, Wis.) to adapt EcoR I at the 5' end of the gene and Not I site at the 3' end, forming a plasmid vector pGA2125. The blasticidin gene was subsequently cloned into a vector pRG1 as shown in FIG. 6, forming plasmid pGA2128. Plasmid vector pRG2130 for gene expression and integration in R, oryzae was then constructed and is shown in FIG. 7, where AmR: ampicillin resistance gene; bsd: antibiotic blasticidin resistance gene; ori: Col El origin; T: fungal transcription terminator $T_{AOX1}$; pk P: R. oryzae pgk1 promoter; and URA3: Pichia pastoris orotidine-5'-phosphate decarboxylase gene. The selectable marker gene provides R. oryzae with resistance to antibiotics, blasticidin. Other antibiotic resistance genes such as sulfanilamide and Gentamycin resistance genes can replace the blasticidin selectable marker gene. The selectable marker gene is placed under the control of R. oryzae pgk1 promoter and a fungal transcription terminator, $T_{AOX1}$, terminates the transcription. In addition, a heterogenous or homogenous URA3 gene or other native gene sequences can be used as integration elements for chromosomal gene insertion. Also, pgk1 promoter sequence can potentially serve as chromosomal integration elements. Chromosomal integration vectors incorporate the desired gene into cell chromosome based on the underlying principle that linearized plasmid DNA fragments are efficiently repaired during fungal transformation by recombination with a homologous DNA restriction fragments.

Closure

While preferred embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An isolated phosphoglycerate kinase gene 1 (pgk1) promoter comprising at least nucleotides 1187–1254 of SEQ ID No. 7.

2. The isolated promoter of claim 1, wherein said promoter comprises the first 1254 base pairs of SEQ ID No. 7.

3. A vector comprising the isolated pgk1 promoter of claim 1.

4. The vector of claim 3, whereby the vector is a plasmid vector.

5. The vector of claim 4, whereby the plasmid vector is a chromosomal integration vector.

6. A process for regulating the expression of a gene coding region, comprising the steps of:
  a. providing a coding region that encodes the gene product;
  b. fusing said coding region to the isolated pgk1 promoter of claim 1 to form a fused promoter/coding region; and
  c. integrating said fused promoter/coding region within genomic DNA of a host cell wherein the promoter regulates the expression of the gene coding region in the host cell.

7. A process for regulating the expression of a gene coding region, comprising the steps of:
  a. providing a coding region that encodes the gene product;
  b. fusing said coding region to the isolated pgk1 promoter of claim 1 to form a fused promoter/coding region;
  c. constructing a plasmid vector comprising said fused promoter/coding region; and
  d. replicating said plasmid vector within a fungal cell such that the said pgk1 promoter regulates the expression of the gene product in the fungal cell.

8. The process of regulating the expression of a gene product according to claim 6 wherein the genomic DNA comprises fungal genomic DNA and wherein the cells comprise fungal cells.

9. The process of regulating the expression of a gene product according to claim 8 wherein the fungal genomic DNA comprises *Rhizopus oryzae* genomic DNA and wherein the fungal cells comprise *Rhizopus oryzae* cells.

10. The process of regulating the expression of a gene product according to claim 6 wherein the genomic DNA comprises plant genomic DNA and wherein the cells comprise plant cells.

11. The process of regulating the expression of a gene product according to claim 7 wherein the fungal genomic DNA comprises *Rhizopus oryzae* genomic DNA and wherein the fungal cells comprise *Rhizopus oryzae* cells.

* * * * *

UNITED STATES PATENT AND TRADEMARK OFFICE
CERTIFICATE OF CORRECTION

PATENT NO. : 6,465,635 B2
DATED : October 15, 2002
INVENTOR(S) : Johnway Gao et al.

It is certified that error appears in the above-identified patent and that said Letters Patent is hereby corrected as shown below:

<u>Column 1,</u>
Line 15, replace "3-phosphogycerate" with -- 3-phosphoglycerate --

<u>Column 4,</u>
Lines 15 and 17, replace "GC TCT AGA" with -- GC <u>TCT AGA</u> --
Line 19, replace "GAT GCA TGC" with -- GAT <u>GCA TGC</u> --
Line 21, replace "GAT GCA" with -- GAT <u>GCA</u> --
Line 22, replace "TGC" with -- <u>TGC</u> --
Line 23, replace "GAT GCA" with -- GAT <u>GCA</u> --
Lines 24 and 26, replace "TGC" with -- <u>TGC</u> --
Line 25, replace "GAT GCA" with -- GAT <u>GCA</u> --
Line 38, replace "correspondent" with -- corresponding --
Line 64, replace "correspondent" with -- correspond --

Signed and Sealed this

First Day of July, 2003

JAMES E. ROGAN
*Director of the United States Patent and Trademark Office*

SEQUENCE LISTING

<160> NUMBER OF SEQ ID NOS: 9

<210> SEQ ID NO 1
<211> LENGTH: 35
<212> TYPE: DNA

-continued

```
<213> ORGANISM: Rhizopus oryzae

<400> SEQUENCE: 1
gctctagaag gttgaggtcg cgaatagaga gcttg                                  35

<210> SEQ ID NO 2
<211> LENGTH: 35
<212> TYPE: DNA
<213> ORGANISM: Rhizopus oryzae

<400> SEQUENCE: 2
gctctagaac ggtaggaaga gcttgaacga tacga                                  35

<210> SEQ ID NO 3
<211> LENGTH: 36
<212> TYPE: DNA
<213> ORGANISM: Rhizopus oryzae

<400> SEQUENCE: 3
gatgcatgct ctcaaaccag tggctgctga ggttga                                 36

<210> SEQ ID NO 4
<211> LENGTH: 36
<212> TYPE: DNA
<213> ORGANISM: Rhizopus oryzae

<400> SEQUENCE: 4
gatgcatgcg cctttggtac tgctcaccgt gctcac                                 36

<210> SEQ ID NO 5
<211> LENGTH: 33
<212> TYPE: DNA
<213> ORGANISM: Rhizopus oryzae

<400> SEQUENCE: 5
gatgcatgct gttaaagtaa ggttctctta taa                                    33

<210> SEQ ID NO 6
<211> LENGTH: 33
<212> TYPE: DNA
<213> ORGANISM: Rhizopus oryzae

<400> SEQUENCE: 6
gatgcatgct atttgaattc gatgccttct cta                                    33

<210> SEQ ID NO 7
<211> LENGTH: 1257
<212> TYPE: DNA
<213> ORGANISM: Rhizopus oryzae

<400> SEQUENCE: 7
tctcaaacca gtggctgctg aggttgaaaa gcttttggga aaacctgtcg aattcaagct        60
tctgaggatg ctattttagc tgcaaagcat ggttgtcaag gtattgtcat ctctaaccat       120
ggtggtagac aattggattt cgcaccttct gctattgaaa ttttgcctga agtcacagct       180
gctcttaagc gagaaagaat taatgaagaa tttgaggttt atattgatgg aggtattcga       240
cgaggtagcg atattttaa agcaattgct ttaggcgcca aggtgtagg cattggacgt        300 ccttctctgg taagcttgcg tacctttaa agcaattgat atttaatgtg cgactagtat       360
gctatgtctt cttatggtga tgctggtgtg gaaaggctct ggaattatt gcaggtaaat       420 ttttttcaca attttggaaa gaagctaact gaaaaataga atgagtttga aatgatcatg       480
```

| | |
|---|---|
| cgcttaatgg gcgtaacatc gattgagcag attaagccag agatggtaga tactcgtaat | 540 |
| ctcaaggatc actttgcttc tattcccaag gattatttgg cagaattagc ctatgatcca | 600 |
| atgcaaccta gatctcattt ttctaagcta taaaacagga aaagatatcc tttaaataaa | 660 |
| gaacagcaat gttttctttc atcattgatg tacacacatt atatttgtac tatatgagca | 720 |
| caacaatcta tttatattgc cttattacag tttagacaac ttactgatac tcattgatta | 780 |
| ttctttgtac gcagacacta accaaacaca ttagttttat accaacctgt gaatttttata | 840 |
| attcagcttg cttaagcttt ccaagtggca tggttttttc tctgatgtcg cgatatcaaa | 900 |
| attcaaaacc gtatcacatc tatcaaacaa aaaaaaaggt gattccaaga tgctatcaga | 960 |
| aatatcaagc taggcttact tttatgttat tcgtttagga agcttcattt tttagaagaa | 1020 |
| gaaaaaaaag agttgaaaat acaaggaaac aagttaaatg ttatacaata agcatgtgct | 1080 |
| ttcataacag aaaggctcct ttagtttaat gaaatcccga tttccatcga acaattaccc | 1140 |
| aataatatta tttgggaaag tgaagtcatg tatgattatt ttttctaat atttatgtca | 1200 |
| agcaaatact tttcttctct tctctttaat ttcaaatacc aattttttcaa cagaatg | 1257 |

<210> SEQ ID NO 8
<211> LENGTH: 558
<212> TYPE: DNA
<213> ORGANISM: Rhizopus niveus

<400> SEQUENCE: 8

| | |
|---|---|
| tacattatat tatgtgagca taacaatcta tttatattgc tttattataa cttagataac | 60 |
| ttactgatac gcattgatta ttctttgtac gcagacacta accaaacacg ttagctttat | 120 |
| acctacctgt gaatttttata attcagcttg cttaagcttt ccaagtggca tggttttttc | 180 |
| tctgatgtcg cgatatcaaa attcaagacc gtatcacatt tatcaaacaa aaaaaaagg | 240 |
| tgactccaag atgttatcag aaatatcaag ccaagtttac tttatattat tcgtttagga | 300 |
| agcttcattt tttagaagaa gaaaaaaaaa gaaagttgaa atacaagga acaagttaa | 360 |
| atgttataca ataagcatgt gctttcataa cagaaaggct cctttagttt aatgaaatcc | 420 |
| cgatttccat cgaacaatta cccaataata tcatttggga aagtgaagtc atgtatgatt | 480 |
| attttttttct tatttatgtc aagcaaatat ttttcttctc ttctctttaa tttcaaatac | 540 |
| caatttttcca acagaatg | 558 |

<210> SEQ ID NO 9
<211> LENGTH: 557
<212> TYPE: DNA
<213> ORGANISM: Rhizopus oryzae

<400> SEQUENCE: 9

| | |
|---|---|
| atatttgtac tatatgagca caacaatcta tttatactgc cttattacag tttagacaac | 60 |
| ttactgatac tcattgatta ttctttgtac gcagacacta accaaacaca ttagttttat | 120 |
| accaacctgt gaatttttata attcagcttg cttaagcttt ccaagtggca tggttttttc | 180 |
| tctgatgtcg cgatatcaaa attcaaaacc gtatcacatc tatcaaacaa aaaaaaggt | 240 |
| gattccaaga tgtatcaga aatatcaagc taggcttact tttatgttat tcgtttagga | 300 |
| agcttcattt tttagaagaa gaaaaaaaag agttgaaaat acaaggaaac aagttaaatg | 360 |
| ttatacaata agcatgtgct ttcataacag aaaggctcct ttagtttaat gaaatcccga | 420 |
| tttccatcga acaattaccc aataatatta tttgggaaag tgaagtcatg tatgattatt | 480 |

-continued

```
tttttctaat atttatgtca agcaaatact tttcttctct tctctttaat ttcaaatacc    540
aatttttcaa cagaatg                                                  557
```